United States Patent
Bieniarz et al.

(10) Patent No.: US 7,541,455 B2
(45) Date of Patent: Jun. 2, 2009

(54) MICROWAVE MEDIATED SYNTHESIS OF NUCLEIC ACID PROBES

(75) Inventors: Christopher Bieniarz, Tucson, AZ (US); Michael Farrell, Tucson, AZ (US); Jerome W. Kosmeder, Tucson, AZ (US); Mark Lefever, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 235 days.

(21) Appl. No.: 11/018,897

(22) Filed: Dec. 21, 2004

(65) Prior Publication Data

US 2005/0158770 A1    Jul. 21, 2005

Related U.S. Application Data

(60) Provisional application No. 60/531,721, filed on Dec. 22, 2003.

(51) Int. Cl.
*C07H 21/02* (2006.01)
*C07H 21/04* (2006.01)
*C12Q 1/68* (2006.01)

(52) U.S. Cl. ................. 536/26.26; 536/26.23; 536/26.8; 435/6

(58) Field of Classification Search ................. 536/26.8, 536/27.11, 28.5; 435/6
See application file for complete search history.

(56) References Cited

U.S. PATENT DOCUMENTS

| | | | |
|---|---|---|---|
| 5,350,686 | A | 9/1994 | Jhingan |
| 5,403,747 | A | 4/1995 | Akins et al. |
| 5,661,040 | A | 8/1997 | Huff et al. |
| 5,684,142 | A | 11/1997 | Mishra et al. |
| 6,673,214 | B1 | 1/2004 | Marchitto et al. |
| 2004/0209303 | A1 | 10/2004 | Martin et al. |

OTHER PUBLICATIONS

Shapiro et al. (I), "Deamination of Cytosine Derivatives by Bisulfite, Mechanism of the Reaction," Journal of the American Chemical Society, 96(3), 906-912 (Feb. 6, 1974).*
Shapiro et al. (II), "Nucleic Acid Reactivity and Conformation. II. Reaction of Cytosine and Uracil with Sodium Bisulfite," Journal of Biological Chemistry, 248(1), 4060-4064 (Jun. 10, 1973).*
Shapiro et al. (III), "Bisulfite-Catalyzed Transamination of Cytosine and Cytidine," Biochemical Biophysical Research Comm., 40(4), 839-843 (Aug. 24, 1970).*
Shabarova et al., "Chemical Properties of Polynucleotides, Modification of Nucleic Acids," Ch. 9 in Advanced Organic Chemistry of Nucleic Acids, VCH Publishers, Inc., New York, NY, 1994, only pp. 389, 410-411 and 425-426 supplied.*
Negishi et al. (I), "N4-Aminocytidine: Formation, Reactivity, and Mutagenicity," Eleventh Symposium on Nucleic Acid Chemistry, Pritchard (ed.), Nucleic Acids Research Symposium Series, No. 12, 29-30, IRL Press, Ltd., Oxford, England, 1983.*
Hartman et al., "Methacrylate Polymerization by AzoRNA: Potential Usefulness for Chromosomal Localization of Genes," Biopolymers, 20(12), 2635-2648 (Dec. 1981).*
Negishi et al. (II), "N4-Aminocytidine, A Nucleoside Analog That Has an Exceptionally High Mutagenic Activity," Nucleic Acids Research, 11(15), 5223-5233 (Aug. 11, 1983).*
Negishi et al. (III), "An Improved Synthesis of N4-Aminocytidine," Chemical & Pharmaceutical Bulletin, 35(9), 3884-3887 (Sep. 1987).*
Hayatsu et al., "The Modification of Nucleosides and Nucleotides. III. A Selective Modification of Cytidine with Semicarbazide," Biochimica et Biophysica Acta, 123(3), 445-457 (Sep. 19, 1966).*
Kikugawa et al., "The Modification of Nucleosides and Nucleotides. V. A Selective Modification of Cytidylic Acids with Girard-P Reagent," Biochimica et Biophysica Acta, 134(1), 221-231 (Jan. 1967).*
Phillips et al., "The Mutagenic Action of Hydroxylamine," in vol. 7 of Progress in Nucleic Acid Research and Molecular Biology, Davidson et al. (eds.), Academic Press, Inc., New York, NY, 1967, only pp. 349-368 supplied.*
Cherouvrier, et al., (2002)—*Tetrahedron Ltrs.*—43:8745-8749.
Dahmani, et al., (1998)—*Tetrahedron Ltrs.*—39:8453-8456.
Meddad, et al., (2001)—*Synthesis*—4:581-584.
Wathey, et al., (2002)—*Drug Discovery Today*—7(6):373-380.
Draper, (1984)—*Nucleic Acids Research*—12(2):989-1002.
International Search Report PCT/US2004/042969, Aug. 24, 2005.

* cited by examiner

*Primary Examiner*—Lawrence E. Crane
(74) *Attorney, Agent, or Firm*—Ventana Medicals Systems, Inc.; Aden A. Rehms

(57) ABSTRACT

A method for preparing a nucleic acid probe is provided. The method comprises forming an activated cytosine or cytidine by a bisulfite catalyzed reaction; and covalently linking a reporter molecule to the activated cytosine or cytidine, wherein said activating step, said covalently linking step, or both are conducted in the presence of microwave energy. Also provided by the invention are nucleic acid probes.

20 Claims, 4 Drawing Sheets

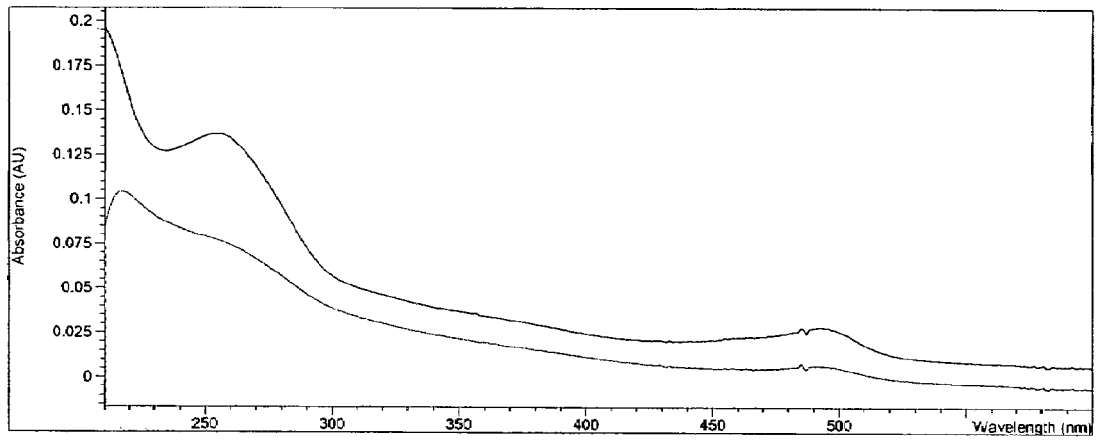
| # | Name | Abs<260nm> | Abs<495nm> |
|---|------|------------|------------|
| 1 | VMSI-1300-73C,C | 7.4337E-2 | 6.4163E-3 |
| 2 | VMSI-1300-73C,MW | 0.13419 | 2.7786E-2 |
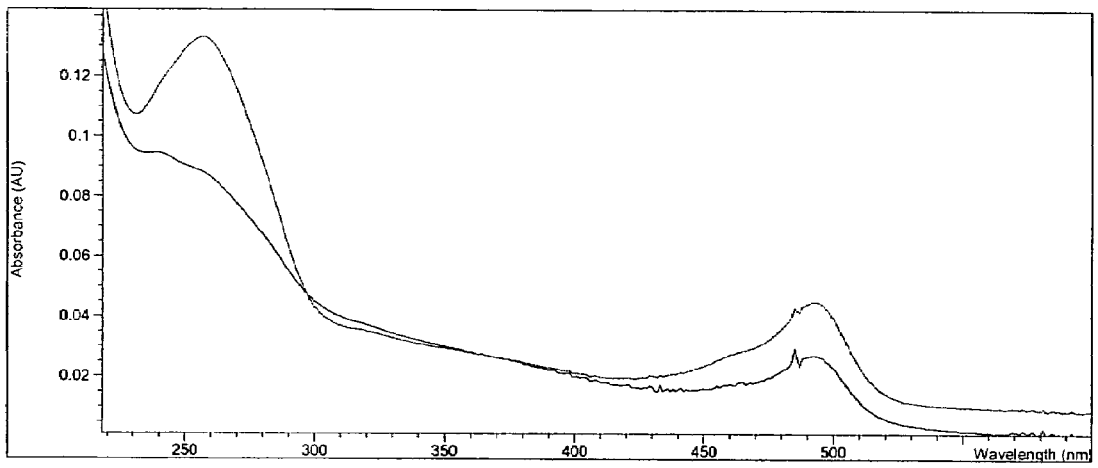
| # | Name | Abs<260nm> | Abs<495nm> |
|---|------|------------|------------|
| 1 | VMSI-1300-74C,MW | 8.6383E-2 | 2.6523E-2 |
| 2 | VMSI-1300-74MW,MW | 0.13166 | 4.4586E-2 |
FIG. 1

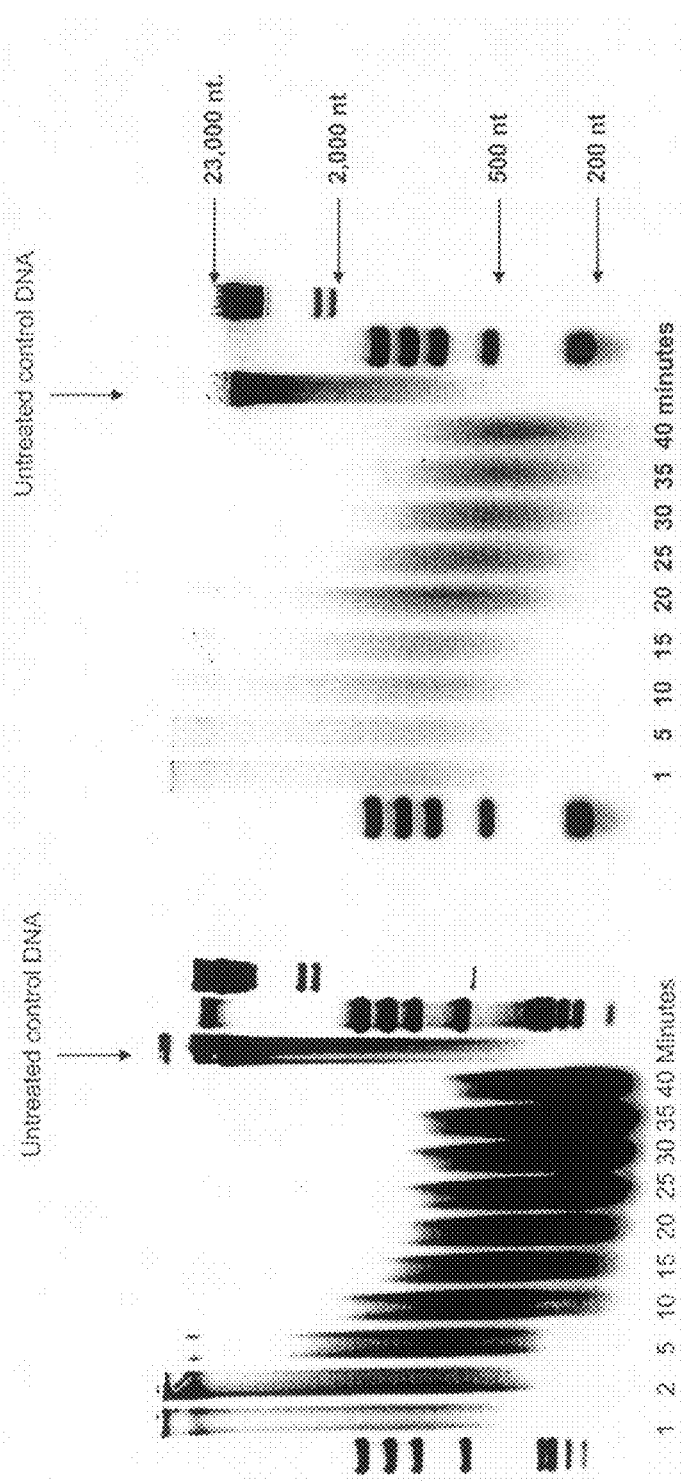

MICROWAVE MEDIATED SYNTHESIS OF NUCLEIC ACID PROBES

CROSS-REFERENCE TO RELATED APPLICATIONS

This application, which was originally published on Jul. 21, 2005 as U.S. Patent Application Publication No. US2005/0158770, claims priority from U.S. Provisional Application Ser. No. 60/531,721, filed Dec. 22, 2003, which provisional application is incorporated herein by reference in its entirety.

BACKGROUND OF THE INVENTION

1. Field of the Invention

The invention relates to nucleic acid probes and to methods for preparing nucleic acid probes.

2. Description of the Related Art

The bisulfite ion-catalyzed displacement of the C4 amine of a cytosine base with 1,2-ethylenediamine is a widely used reaction for the conversion of an unreactive C4 cytosine amine into a reactive aliphatic amine. The resulting aliphatic amine has been used to label DNA with suitable markers or reporter groups, such as fluorophores, chromogens, haptens, proteins, and so on. In addition, the reaction has also been used for the conversion of cytosine residues into uracils and thymidines.

Despite its widespread use, the reaction suffers from several disadvantages. For instance, the bisulfite activation step is very slow and inconvenient, taking place over several days. Further, the linker on the distal amine is generally of limited length, which can interfere with the hybridization process, resulting in depression of the sensitivity of the probe. In addition, because the modified reporter must present an electrophilic group, such as active ester or an isocyanate, competing reactions with water can depress yield, and result in the number of desirable reporter groups being too small to provide efficient signal generation.

Microwave energy has been used to accelerate chemical reactions in synthetic organic chemistry. Microwave energy has not been previously used, however, in biochemical reactions involving modification of nucleic acids, antibodies, enzymes, other proteins, or lipids.

In view of the disadvantages discussed above, and other disadvantages, a need exists for new nucleic acid probes, and for improved methods of preparing nucleic acid probes.

SUMMARY OF THE INVENTION

In one embodiment, the invention relates to a method for preparing a nucleic acid probe, the method comprising the steps of: forming an activated cytosine or cytidine by a bisulfite catalyzed reaction; and covalently linking a reporter molecule to the activated cytosine or cytidine, wherein said activating step, said covalently linking step, or both are conducted in the presence of microwave energy. The invention also relates to a nucleic acid probe prepared according to the method of the first embodiment.

In another embodiment, the invention relates to a method for preparing a nucleic acid probe of formula I:

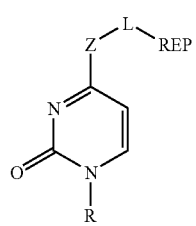

(I)

wherein,
R is H or a biomolecule;
Z is a nucleophilic group;
L is a linker; and
REP is a detectable reporter group, said method comprising the steps of:
(a) forming an activated cytosine or cytidine group of formula (II) by a bisulfite based reaction

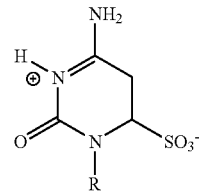

(II)

(b) covalently linking a reporter containing group to the activated group of formula (II), to form the probe of formula I, wherein step (a), step (b), or both step (a) and step (b) are conducted in the presence of microwave energy. The invention also provides a nucleic acid probe of formula (I) prepared according to the method of the second embodiment.

In a further embodiment, the invention relates to a method for preparing a nucleic acid probe of formula III:

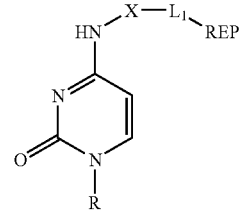

(III)

wherein,
R is H or a biomolecule;
X is NH, NHCONHNH, NHCSNHNH, NHCS, NHCO, or —O—;
$L_1$ is a hydrophilic linker; and
REP is a detectable reporter group, said method comprising the steps of:
(a) forming an activated cytosine or cytidine group of formula (IV) by a bisulfite based reaction

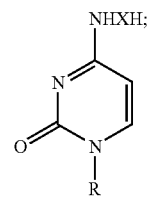

(IV)

and
(b) covalently linking a reporter containing group to the activated group of formula (IV), to form the probe of formula III, wherein step (a), step (b), or both step (a) and step (b) are conducted in the presence of microwave energy. The invention also provides a nucleic acid probe of formula (III) prepared according to the method of the second embodiment.

In another embodiment, the invention relates to a method for preparing an activated group of formula (II):

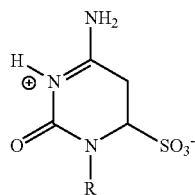

wherein R is H or a biomolecule, said method comprising activating a cytosine or cytidine group by a bisulfite based reaction to provide an activated cytosine or cytidine group of formula (II), wherein said activating step is conducted in the presence of microwave energy. The invention also provides an activated group of formula (II) prepared according to the fourth embodiment.

In a yet further embodiment, the invention provides cytosine or cytidine derivatives of formula (IV-A):

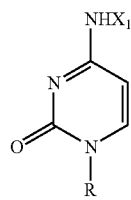

wherein R is H or a biomolecule, and $X_1$ is $NH_2$, $NHCONHNH_2$, $NHCSNHNH_2$, $NHCSNH_2$, $NHCONH_2$, $NH-Q-NHNH_2$ or $NHCO-Q-CONHNH_2$ where Q is a linker, preferably a repeating oxyalkyl linker, more preferably a PEG linker such as —$(OCH_2CH_2)_n$—, where n is 2 to 30. The invention also provides a method for preparing a derivative of formula (IV-A), the method comprising: activating a cytosine or cytidine group by a bisulfite based reaction to provide formula (IV-A), wherein said activating step is conducted in the presence of microwave energy. The invention also provides an activated group of formula (IV-A) prepared according to this method.

In another embodiment, the invention relates to a nucleic acid probe of formula (X):

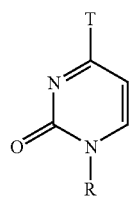

wherein R is H or a biomolecule; and
T is a fluorophore containing dendrimer or a fluorophore containing polymer. The invention also provides methods for preparing compounds of formula (X).

In a still further embodiment, the invention provides compounds of the formula:

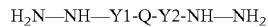

wherein,
Q is a repeating oxyalkyl group; and
Y1 and Y2 are independently a bond or —C(O)—.

BRIEF DESCRIPTION OF THE DRAWINGS

FIG. 1 depicts UV/Vis spectra of various probes prepared according to the invention.
FIG. 3 depicts DNA separated in a gel, that has been cleaved in a microwave reactor at 100 degrees.
FIG. 4 depicts DNA separated in a gel, that has been cleaved thermally at 100 degrees.

DETAILED DESCRIPTION OF THE INVENTION

Figure 2:
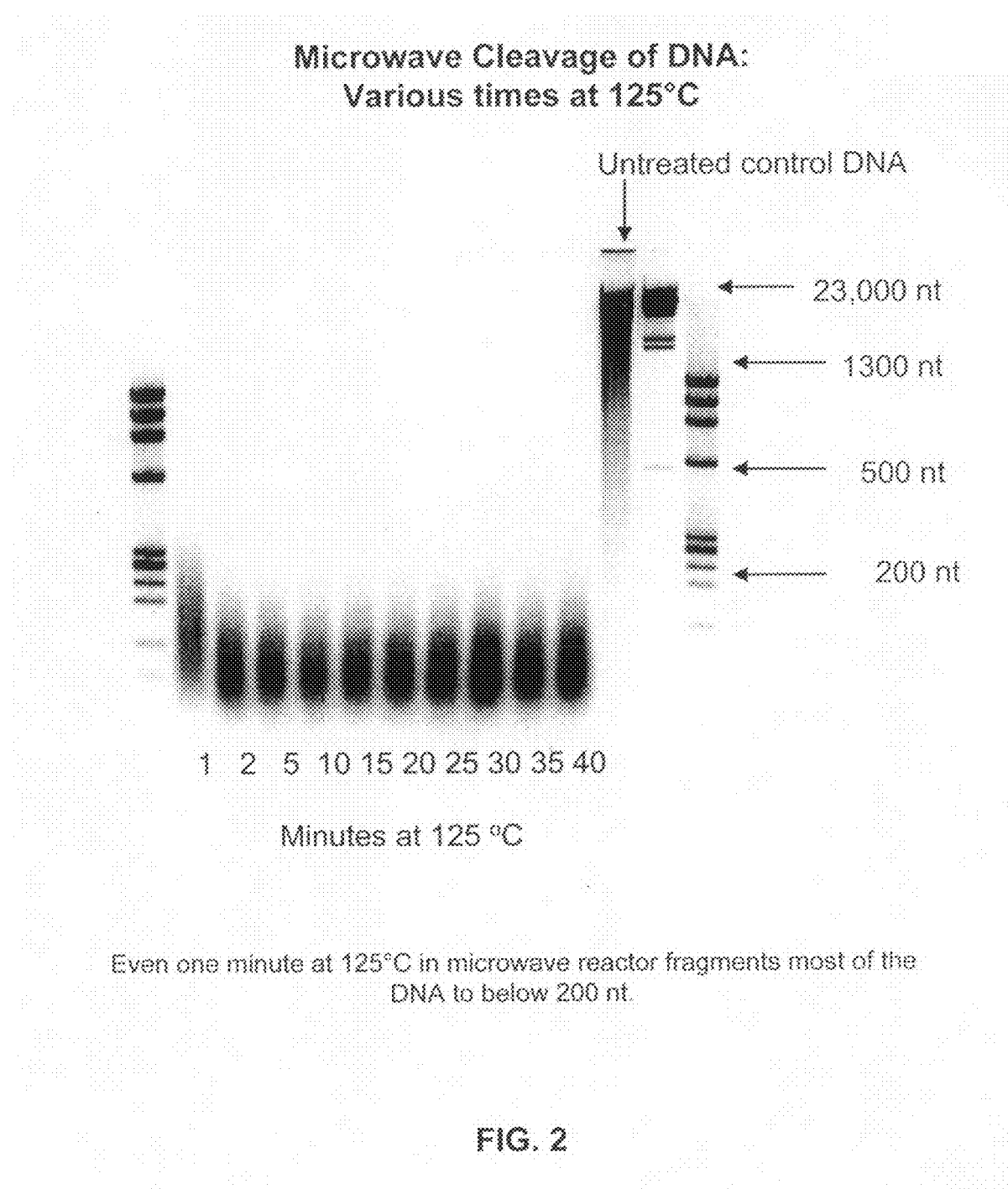
FIG. 2 depicts DNA separated in a gel, that has been cleaved in a microwave reactor at 125 degrees.

In a first aspect, the invention provides a method for preparing a labeled cytosine, a labeled cytidine, or labeled cytidine-containing biomolecule, such as oligonucleotides, DNA molecules, RNA molecules, proteins, peptides, or other biomolecules. Generally, the method comprises the steps of forming an activated cytosine or cytidine by a bisulfite catalyzed reaction, and covalently bonding a reporter group to the activated cytosine or cytidine. The activating step, the covalently bonding step, or both, are carried out in the presence of microwave energy. The steps of the method can be carried out separately, or in a one pot reaction.

In one embodiment, the invention relates to, a method for preparing a nucleic acid probe of formula I:

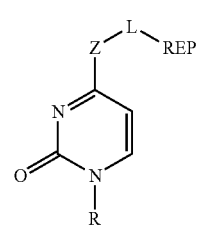

wherein, R is H or a biomolecule; Z is a nucleophilic group; L is a linker; and REP is a detectable reporter group. The method comprises:

(a) forming an activated cytosine or cytidine group of formula (II) by a bisulfite based reaction

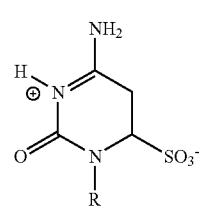

(b) covalently linking a reporter containing group to the activated group of formula (II), to form the probe of formula I. Step (a), step (b) or both steps (a) and (b) are conducted in the presence of microwave energy. This embodiment is depicted in Scheme 1A.

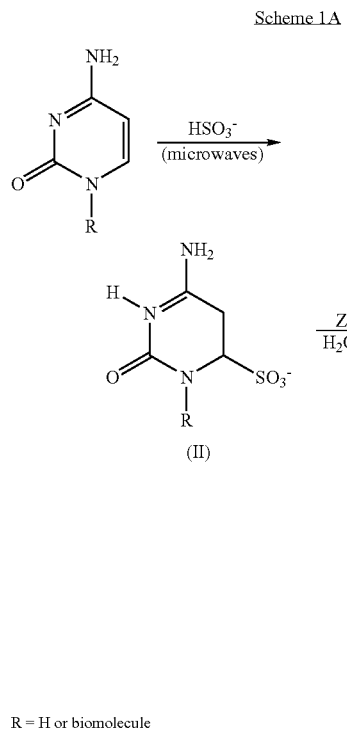

R = H or biomolecule

In this embodiment, a cytidine or cytosine is activated in the presence of bisulfite to form an activated moiety presenting a primary amine group. The activated moiety is reacted with a group containing a detectable reporter, represented in Scheme 1A by Z-L-Rep. Either or both of the two steps is conducted in the presence of microwave energy.

Z in Scheme 1A represents a nucleophilic group. Examples of useful nucleophilic groups include $NHNH_2$, $NHCONHNH_2$, $NHCSNHNH_2$, $CONHNH_2$, $NHOH$, and other super nucleophilic groups and amines.

L represents a linker. For instance, L is a hydrophilic linker. Preferred linkers include linear or branched repeating oxyalkyl groups, such as polyethylene glycol (PEG). An example of a preferred linker is $-(OCH_2CH_2)_n-$, wherein n is 2 to 30. Examples of other useful linkers include linear aliphatic, mixed aliphatic-aromatic, aromatic, alicyclic, heteroaromatic, heteroalicyclic, and the like groups. The linker may contain, for example at its ends, any functional groups suitable for bonding to Z and to REP. Suitable functional groups include $NHNH_2$, $NHCONHNH_2$, $NHCSNHNH_2$, $CONHNH_2$, $NHOH$.

An advantage of the PEG linker is its solubilizing effect. For instance, it has been discovered that when 5-80% v/v of various molecular weights of PEG are present, the PEG, because of its aqueous solubility, allows the process to be carried out in an aqueous medium and results in a homogenous reaction solution. As a result, the formation of labeled probes occurs with greater yield than is possible with heterogeneous processes, and can result in the incorporation of fluorophores well in excess of 5-6%, thus providing brighter and more sensitive detection of the fluorophore than in known systems.

The reporter group ("REP") is any detectable moiety commonly used for labeling probes. Examples include fluorophores, chromogens, haptens, proteins such as enzymes, nanoparticles such as dendrimers, fullerenes, and fullerene related structures, nanocrystals, and so on. Preferred examples include 2,4-dinitrophenyl (DNP) group, fluorescein and biotin. Quantum dots may also be introduced into nucleic acid probes using the method of the invention. Quantum dots are a technology useful for labeling probes, where detection is based on the high quantum yields, non-photobleachable fluorophores composed of sulfides and selenides of certain transition metals. Such materials are available, for example, from Quantum Dot Corporation, Hayward, Calif.

In another embodiment, the invention relates to a method for preparing a nucleic acid probe of formula III:

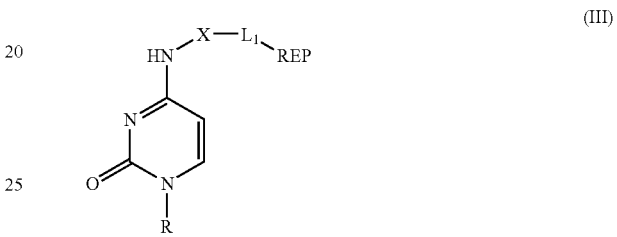

wherein, R is H or a biomolecule; X is NH, NHCONHNH, NHCSNHNH, NHCS—, NHCO—, or —O—; $L_1$ is a hydrophilic linker; and REP is a detectable reporter group. The method comprises (a) forming an activated cytosine or cytidine group of formula (IV) by a bisulfite based reaction

and (b) covalently linking a reporter containing group to the activated group of formula (IV), to form the probe of formula III, wherein step (a), step (b), or both step (a) and step (b) are conducted in the presence of microwave energy. This embodiment is depicted in Scheme 1B.

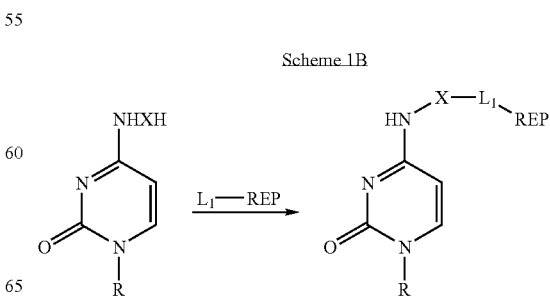

X is NH, NHCONHNH, NHCSNHNH, NHCS—, NHCO—, or —O—. Preferred X groups include NH and NHCO. A particularly preferred X is NH.

$L_1$ represents a hydrophilic linker containing a moiety capable of coupling with the nucleophile NHX, such as an electrophilic group. Preferred hydrophilic linkers include linear or branched repeating oxyalkyl group, such as polyethylene glycol (PEG). An example of a preferred hydrophilic linker is $(OCH_2CH_2)_n$, wherein n is 2 to 30. Preferred electrophilic groups on $L_1$ include active esters, isocyanates, and activated aromatic halides. An example of the synthesis of a PEG containing cytidine is depicted in Scheme 2.

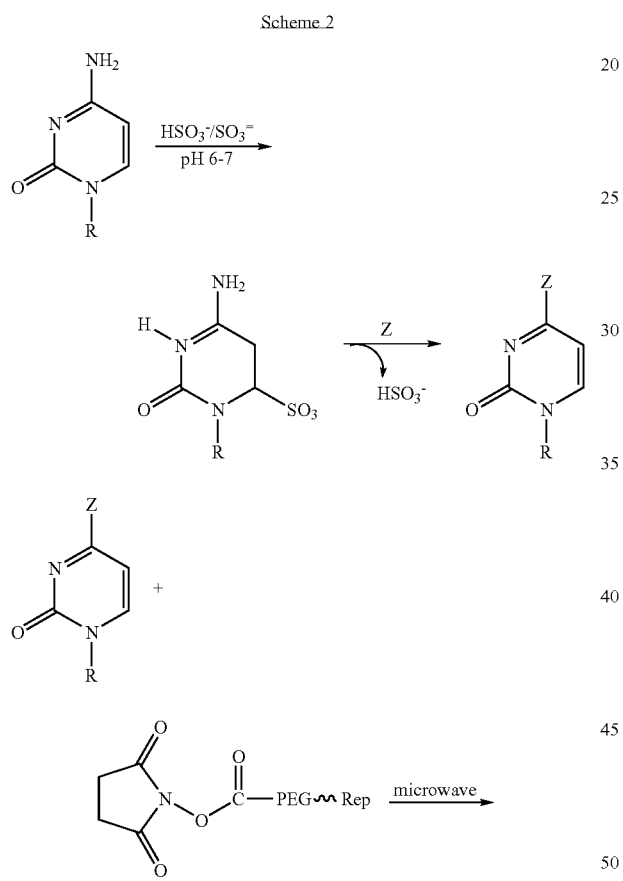

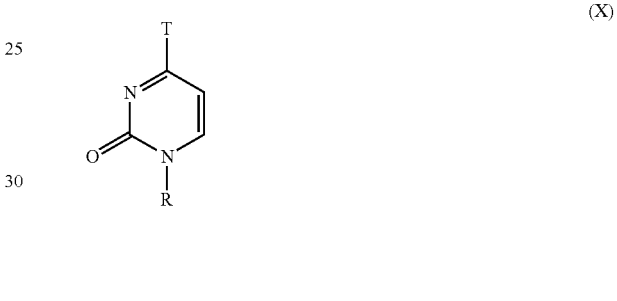

In the methods of the invention, any microwave source can be used to provide the microwave energy, for example, light energy having a wavelength between about 1 millimeter and 1 meter, such as a wavelength of about 12.2 cm. Commercial microwave synthesizers, such as those available from CEM Corporation, Matthews, N.C., may be used.

The microwave mediated reactions of the invention are preferably conducted at a pH of about 4.5 to about 7. Polar aprotic solvents, such as dimethyl sulfoxide, dimethylformamide, formamide, acetonitrile, and/or ketones, may also be present to aid in solubilizing the fluorophores. The reaction is preferably conducted for about 10 to 60 minutes, at between about 50 to 130° C. The labeled product can be recovered by known methods.

In addition to the reporter groups discussed above, dendrimers that are functionalized with multiple fluorophores and nucleophilic group(s) may also be used in the invention. Functionalized dendrimers provide amplified fluorescence due to the multiplicity of fluorophores present thereon.

In a further embodiment, therefore, the invention relates to a nucleic acid probe of formula (X):

(X)

[structure]

wherein R is H or a biomolecule; and

T is a fluorophore containing dendrimer or a fluorophore containing polymer. The invention also provides methods for preparing compounds of formula (X).

The dendrimers of this embodiment can be transaminated onto cytosines through a free amine on the dendrimer. A general example of a functionalized dendrimer is depicted in Scheme 3A. A specific example of a preferred dendrimer (prior to fluorophore functionalization) is shown in Scheme 3B. The Scheme 3B dendrimer is available from Dendritech, Inc., Midland, Mich.

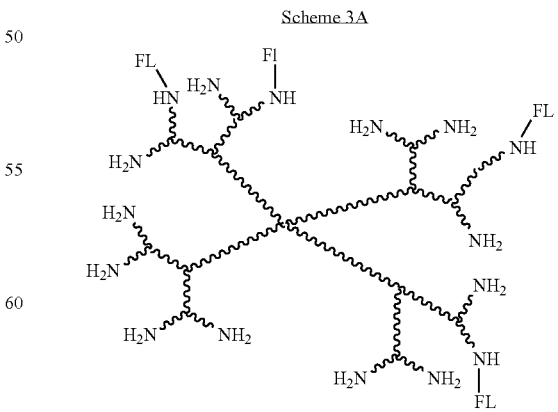

FL = fluorophore

Scheme 3B
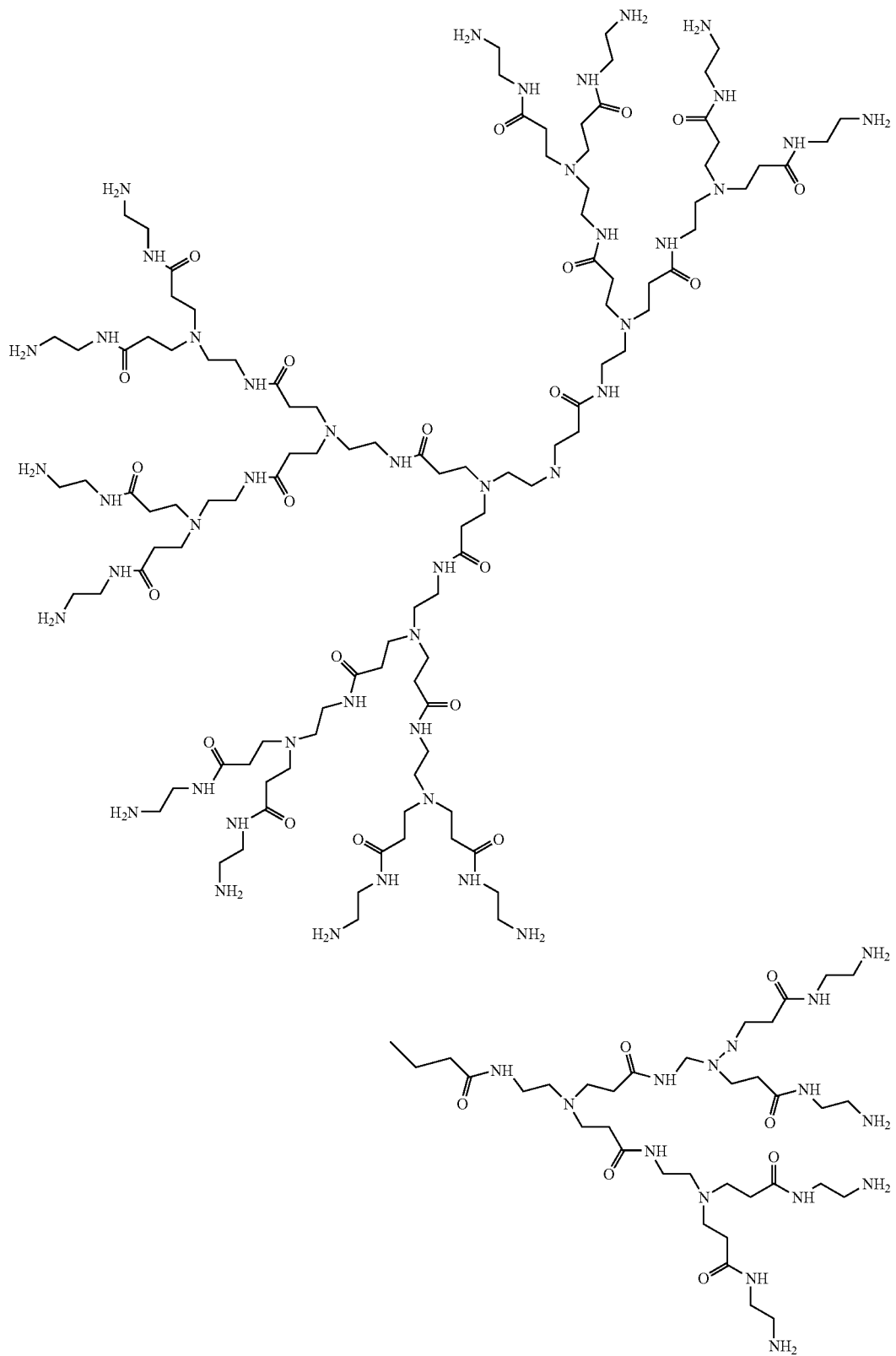

Linear polymers that are functionalized with fluorophores and nucleophilic group(s) may also function as useful reporter containing moieties. Examples of such polymers are described in U.S. Pat. No. 5,661,040, which is incorporated herein by reference in its entirety. Shorter, water-soluble polacrylamide hydrazide polymers (PAH) were also synthesized. A preferred functionalized polymer is polyacrylamide hydrazide functionalized with fluorophores, particularly PAH of MW 10,000 to 20,000 bearing between 10 to 40 hydrazide groups per polymer chain.

The present invention provides several advantages over the prior art. For instance, the invention provides a high yield of the desired product, allows the introduction of reporter groups into more than 6% of the cytosine groups in a nucleic acid, allows ready hybridization between the labeled probe and the target, and is extremely rapid, allowing the labeling of probes with reporter groups within minutes rather than days, as in conventional methods. A further advantage is that nucleic acids derivatized according to the method of the invention can be simultaneously sheared and fragmented into smaller probe sized units, through the application of heat, microwave energy, and pressure.

In a second aspect, the invention provides compounds that are useful as nucleic acid probes and/or in the preparation of nucleic acid probes.

Thus, in one embodiment, the invention provides cytosine or cytidine derivatives of formula (IV-A):

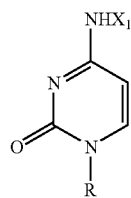

(IV-A)

wherein R is H or a biomolecule, and $X_1$ is $NH_2$, $NHCONHNH_2$, $NHCSNHNH_2$, $NHCSNH_2$, $NHCONH_2$, $NH$-Q-$NHNH_2$ or $NHCO$-Q-$CONHNH_2$ where Q is a linker, preferably a repeating oxyalkyl linker, more preferably a PEG linker such as $—(OCH_2CH_2)_n—$, where n is 2 to 30.

Included within this embodiment, are derivatives of the formula IV-A-1:

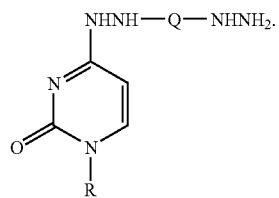

(IV-A-1)

Also included within this embodiment, are derivatives of the formula IV-A-2:

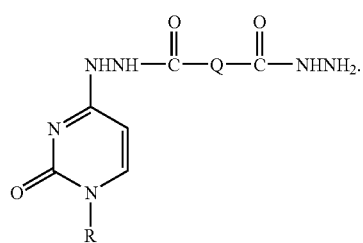

(IV-A-2)

The invention also provides a method for preparing a derivative of formula (IV-A), the method comprising: activating a cytosine or cytidine group by a bisulfite based reaction to provide formula (IV-A), wherein said activating step is conducted in the presence of microwave energy. The invention also provides an activated group of formula (IV-A) prepared according to this method.

In another embodiment, the invention provides probes of the formula (V):

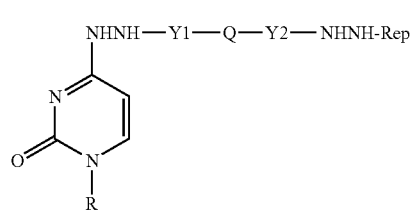

(V)

wherein
R is H or a biomolecule;
Q is a repeating oxyalkyl group;
Y1 and Y2 are independently a bond or $—C(O)—$; and
Rep is a detectable reporter group.

Preferred compounds of formula (V) include those wherein Y1 and Y2 are each a bond.

Preferred compounds of formula (V) include those wherein Y1 and Y2 are each $—C(O)—$.

Rep, the detectable reporter group, is as defined above. Preferred reported groups include fluorophores, chromogens, haptens, proteins, and so on. Particularly preferred are 2,4-dinitrophenyl (DNP) group, fluorescein and biotin.

Q is a repeating oxyalkyl group. By repeating oxyalkyl is meant a group containing at least two alkyl moieties, connected by an oxygen atom. The alkyl moieties may be linear or branched. Preferred Q include polyethylene glycol, including groups of the formula $—(OCH_2CH_2)_n—$, wherein n is 2 to 30.

In a further embodiment, the invention provides compounds of the formula (XX), which are useful, for example, as linkers in nucleic acid probes:

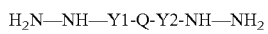

$H_2N—NH—Y1$-Q-$Y2$-$NH—NH_2$ (XX)

wherein,
Q is a repeating oxyalkyl group; and
Y1 and Y2 are independently a bond or $—C(O)—$.

Preferred compounds of formula (XX) include those wherein Y1 and Y2 are each a bond.

Preferred compounds of formula (XX) include those wherein Y1 and Y2 are each $—C(O)—$.

Preferred Q include polyethylene glycol, including groups of the formula $—(OCH_2CH_2)_n—$, wherein n is 2 to 30.

The invention also encompasses compounds of the formula XX-A:

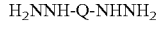

$H_2NNH$-Q-$NHNH_2$ (XX-A)

wherein Q is a repeating oxyalkyl group. Preferably, Q is $—(OCH_2CH_2)_n—$, wherein n is 2 to 30.

The invention also encompasses compounds of the formula XX-B:

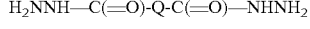

$H_2NNH—C(=O)$-Q-$C(=O)—NHNH_2$ XX-B wherein Q is a repeating oxyalkyl group. Preferably, Q is $—(OCH_2CH_2)_n—$, wherein n is 2 to 30.

The following examples are illustrative of various aspects of the invention but do not serve to limit its scope.

EXAMPLES

General

Herring DNA for Labeling Experiments

Double stranded herring DNA, which had previously been sonicated to a mean size of about 500 nucleotides long, was precipitated with ethanol, washed three times with 80% ethanol and dissolved in water to a concentration of 10 mg/mL.

Single stranded DNA was generated by denaturing in a boiling water bath. Aliquots (50 µL) of herring DNA (10 mg/mL) were placed in screw-cap microcentrifuge tubes and denatured by immersing in a boiling water bath for 10 minutes followed by freezing in a dry ice-ethanol bath. The tubes were stored at −80° C. until used for labeling experiments.

Calculation of the Percentage of Nucleotides Labeled with Fluorescein

The extinction coefficient is defined as the optical absorbance at a given wavelength of a 1M solution in a 1 cm light path at a given pH.

For double-stranded DNA at a concentration such that the total nucleotide concentration is 1M at pH 7.4 the optical absorbance at 260 nM is 6,600. In other words the extinction coefficient at 260 nM is 6,600. By measuring absorbance at 260 nM then one can calculate the molarity of nucleotides in the solution:

$$M_{(Nuc)} = A_{(260)}/6,600$$

where $A_{(260)}$ is the absorbance of the solution to be measured and $M_{(Nuc)}$ is the molarity of nucleotides in that solution. $M_{(Nuc)}$ is determined by measuring $A_{(260)}$ and calculating $M_{(Nuc)}$.

For Fluorescein attached to DNA the extinction coefficient at 495 nM is 30,000. The concentration of Fluorescein can be determined by measuring absorbance at 495 nM and calculating it's molarity:

$$M_{(F)} = A_{(495)}/30,000$$

where $A_{(495)}$ is the absorbance of the solution to be measured and $M_{(F)}$ is the Molarity of Fluorescein in that solution.

When fluorescein is present in a DNA solution whose absorbance at 260 nM is to be measured, it is necessary to take into account the fact that fluorescein also absorbs at 260 nM. The contribution of fluorescein to such an A260 measurement can be calculated using measurements of fluorescein absorbance at 260 nM and 495 nM when the amount of DNA present is known from other measurements. This information is available to the person of skill in the art (see for example, the website of Molecular Probes Inc.).

The absorbance at 260 nM by DNA-bound fluorescein is equal to the absorbance at 495 nM multiplied by 0.32:

$$A_{(260F)} = A_{(495)} X(0.32)$$

This absorbance is subtracted from the total absorbance at 260 nM to get the DNA's absorbance contribution at that wavelength:

$$A_{(260\,DNA)} = A_{(260\,Total)} - A_{(495)} X(0.32)$$

This gives a corrected $A_{(260\,DNA)}$ which is used to calculate the DNA concentration in moles of nucleotide per liter as shown above. No correction is needed for the absorbance of DNA at 495 nM.

When DNA concentration is known in Moles nucleotide per liter [$M_{(Nuc)}$] and Fluorescein concentration is known in moles per liter of fluorescein [$M_{(F)}$] then the fraction of nucleotides labeled is also known:

Percent nucleotides labeled=100 $XM_{(F)}/M_{(Nuc)}$

% nucleotides labeled=(100 $XA_{(495)}/30,000)/(A_{(260\,Total)} - (A_{(495)} X0.32)/6,600)$.

Example 1

Microwave-Assisted Synthesis of Hydrazine-Modified ssDNA (a) Preparation of Transamidation Solution In a 50 mL conical tube, sodium bisulfite (1.06 g, 10 mmoles), sodium phosphate, monobasic (1.38 g, 10 mmoles) and hydroquinone (110 mg, 1 mmole) were dissolved in approximately 5 mL deionized water. To this solution was added hydrazine hydrate (1.5 mL, 30 mmoles) under ice cooling to give a pH of 8.7. The pH was adjusted with concentrated hydrochloric acid to pH of 7.2. This solution was used immediately and the remainder discarded.

(b) Microwave-Assisted Hydrazinolysis of Herring Sperm ssDNA

The transamidation solution (500 µL) and ssDNA (20 µg) were microwaved in a heavy-wall glass tube (CEM Corporation, 908035) fitted with a stirbar and Teflon-lined silicone septum pressure cap, for one hour at 50° C. (50 W, 50 psi max, 30 s ramp) using a commercial microwave synthesizer (Discovery, CEM Corporation). The pH of the reaction solution was raised by addition of 200 µL of 1M CAPS, pH 10, and heated to 50° C. in a circulating water bath for 15 minutes.

(c) Purification of Modified ssDNA

The modified ssDNA was isolated by capture on glass-fiber columns (QIAprep Spin Columns, 27106, Qiagen Corporation) according to manufacturer's directions. In short, the reaction solution was diluted with five volumes of binding buffer (PB) and passed through a QIAprep spin column using a vacuum manifold. The column was washed with 500 µL PB buffer, then with 10×500 µL PE (wash) buffer. The column was centrifuged for one minute at 13,000 g, discarding the residual PE buffer. The ssDNA was eluted with 100 µL EB buffer by centrifuging 13,000 g for one minute. Alternatively, the DNA was purified by dialysis followed by repeated precipitation with isopropanol.

Example 2

Microwave-Assisted Synthesis of Fluorescein-5-thiocarbamo-DNA

In a heavy-wall glass tube (CEM Corporation, 908035), hydrazine-modified herring DNA (5 µg in 100 µL EB buffer) was mixed with 200 µL 1M CAPS, pH 10 and 300 µL fluorescein-5-isothiocyanate (FITC) (20 mg/mL DMSO). The solution was microwaved for 30 minutes at 50° C. (50 W, 50 psi max, 30 s ramp). The DNA was purified by capture on glass-fiber columns (QIAprep Spin Columns, 27106, Qiagen Corporation) according to manufacturer's directions. In short, the reaction solution was diluted with five volumes of binding buffer (PB) and passed through a QIAprep spin column using a vacuum manifold. The column was washed with 500 µL PB buffer, then with 10×500 µL PE (wash) buffer, or until no fluorescence was detected in the wash. The column was centrifuged for one minute at 13,000 g, discarding the residual PE buffer. The ssDNA was eluted with 100 µL EB buffer by centrifuging 13,000 g for one minute. The incorporation of fluorescein was determined using the absorption of the modified DNA at 260 and 495 nm and the equation found in Talavera, et al., J. Photochem. Photobiol. B 59, 9 [2000].

Table 1 below provides a comparison of the percentage of fluorescein incorporation, using microwave heating, as described in Examples 1 and 2, compared with thermal heating:

TABLE 1

Thermal vs. Microwave 2-step FITC Labeling Results

| | % Nucleotides Labeled |
|---|---|
| Thermal Hydrazinolysis/Thermal FITC Incorporation | 1.95% |
| Thermal Hydrazinolysis/Microwave FITC Incorporation | 7.49% |
| Microwave Hydrazinolysis/Thermal FITC Incorporation | 4.88% |
| Microwave Hydrazinolysis/Microwave FITC Incorporation | 8.36% |

FIG. 1 depicts UV-Visible spectra of modified DNA conjugates prepared according to examples 1 and 2. The UV-Vis spectra are of direct labeled DNA. The DNA was modified with hydrazine to produce N4-aminocytidines, which were then reacted with FITC (fluorescein isothiocyanate) The four spectra illustrate the differences and lack of differences in the product between using thermal and microwave heating to incorporate hydrazine as a linker and FITC as a fluorescent marker.

Example 3

Labeling by Bisulfate Transmission Using Fluorescein Hydrazide in a Microwave Reactor A bisulfite solution was made by dissolving 1.56 g $NaHSO_3$ and 0.64 g $Na_2SO_3$ in 4.3 ml of water. Hydroquinone, 200 ul of a fresh 50 mM solution, was added to yield the activation solution.

300 ul of the activation solution was added to 100 ul of ssDNA (50 ug total) solution in water containing 10 mg/ml Fluorescein hydrazide (1 mg total) in a microwave reactor tube which was then sealed. (Stock DNA is fragmented herring DNA at a concentration of 10 mg/ml in water, denatured by immersing in boiling water bath for 10 minutes followed by freezing in a dry ice ethanol bath and stored at minus 80° C.) The sealed reactor tube was placed in the microwave reactor which was then run at 80° C. for 10 min.

After cooling the DNA was diluted by adding 5 volumes of Qiagen solution PB and purified on a Qiagen spin column. Five washes with PB were followed by 5 washes with Qiagen solution PE and elution in EB. Optical absorbance was measured at 260 nM and 495 nM and percent nucleotides labeled by fluorescein was calculated. 3.5% of the nucleotides were labeled.

Example 4

DNA Cleavage Experiments

These experiments compared the extent of cleavage of DNA treated with microwaves, as compared with DNA that is thermally treated only. The results are illustrated in FIGS. 1-3. The results indicate that the extent of DNA cleavage is much greater with microwave treatment, than with thermal treatment alone.

A. DNA Cleavage in Microwave Reactor at 125 Degrees

A solution (400 ul) of high molecular weight Salmon DNA at a concentration of 2 mg/ml in TE was placed in a microwave reactor tube (no stirring bar). The tube was placed in a microwave reactor and the mixture heated to 125 degrees for 1 minute and fast cooled. A 10 ul aliquot was removed, and the tube resealed and returned to the reactor. This cycle of heating, cooling and sample-taking was repeated for a total of 10 times.

From each 10 ul aliquot 3 ul was taken, mixed with 25 ul sample buffer and 15 ul of this was applied to a 2% agarose gel in 1×TAE with molecular weight standards Lambda (HindIII) and phiX174 (HaeIII) and untreated DNA. The gel is shown in FIG. 2.

B. DNA Cleavage in Microwave Reactor at 100 Degrees

A solution (400 ul) of high molecular weight Salmon DNA at a concentration of 2 mg/ml in Tris/HCl pH 7.4 (1 mM) and EDTA (0.1 mM) was placed in a microwave reactor tube (no stirring bar). The tube was placed in a microwave reactor, heated to 100 degrees for 1 minute and fast cooled. A 10 ul aliquot was then removed and stored on ice, and the reactor tube resealed, returned to the reactor and heated for 4 minutes at 100 degrees. This cycle of heating, cooling and sample-taking was repeated for a total of 10 times. Samples were taken after microwaving for totals of 1, 5, 10, 15, 20, 25, 30, 35, and 40 minutes.

From each 10 ul aliquot 3 ul was removed, mixed with 25 ul sample buffer and 15 ul of this was applied to a 2% agarose gel in 1×TAE with m.w. standards Lambda (HindIII) and phiX174 (HaeIII) and untreated DNA. Gel was subjected to electrophoresis at 80 volts till bromophenol blue marker had progressed ⅔ of the distance to the end of the gel. The gel is shown in FIG. 3.

C. DNA Cleavage by Heat at 100 Degrees

A solution (400 ul) of high molecular weight Salmon DNA at a concentration of 2 mg/ml in Tris/HCl pH 7.4 (1 mM) and EDTA (0.1 mM) was placed in a 2 ml microcentrifuge tube with a screw cap. The tube was placed in a boiling water bath for 1 minute and fast cooled. A 10 ul aliquot was removed and stored on ice, and the tube resealed and returned to the boiling water bath. This cycle of heating, cooling and sample-taking was repeated for a total of 10 times. Samples were taken after heating for totals of 1, 5, 10, 15, 20, 25, 30, 35, and 40 minutes.

From each 10 ul aliquot 3 ul was taken, mixed with 25 ul sample buffer and 15 ul of this was applied to a 2% agarose gel in 1×TAE with m.w. standards Lambda (HindIII) and phiX174 (HaeIII) and untreated DNA. Gel was subjected to electrophoresis at 80 volts till bromophenol blue marker had progressed ⅔ of the distance to the end of the gel. The gel is shown in FIG. 4.

Example 5

Bisulfite Catalyzed DNA Labeling by a DNP-PEG-hydrazine

This example demonstrates a single step process for installing a probe directly on a nucleic acid. To prepare bisulfite with the chaotrope, trifluoroacetic acid (TFA), 1.53 ml of TFA is added to 2.5 ml of D.I. water on ice and the mixture is allowed to cool for ten minutes. The DNP-PEG hydrazine is added so that the final concentration would be 10 mM, after neutralization with NaOH pellets. After dissolution of the hydrazine the solution is warmed to room temperature and 0.531 g (5.0 mmol) of sodium. bisulfite added. The solution is then vortexed until all of the bisulfite has dissolved. The pH is adjusted to pH 7.1 using a combination of solid and 10 N NaOH and the volume adjusted to 3.60 ml with D.I. water. (2 pellets plus 5 to 10 drops 10N NaOH). A 100 mg/ml solution of hydroquinone in absolute ethanol is prepared and added to the bisulfite buffer at 50 µl of hydroquinone solution per 5 ml of bisulfite buffer. The final concentration of hydrazine is 10 mM. Procedure: To a frozen sample of 200 µg of denatured salmon DNA in 100 µl of D.I. water is added 3.6 ml of the above solutions to get identical DNA solutions but with 3 different concentrations of DNP-PEG hydrazine. Each solution is then split into two 1.8 ml aliquots. One tube containing each hydrazine concentration is incubated at 45 degrees in a water bath for 4 days. Each of the other three tubes is reacted in the microwave for 30 min at 45 degrees.

After each reaction the sample is dialysed against water several times. The DNA is recovered by iso-propanol precipitation. DNP-PEG-hydrazine is removed by repeatedly precipitating the DNA with isopropanol and washing with 80% ethanol.

Example 6

Bisulfate Hydrazine DNA Adduct in Presence of Trifluoroacetate

This example demonstrates a two step process for installing a probe on a nucleic acid.

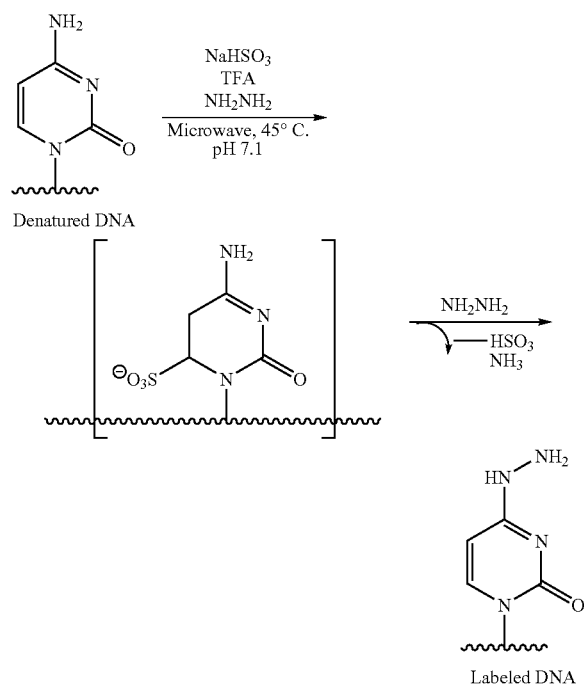

Denatured DNA

Labeled DNA

To prepare bisulfite with the chaotrope, trifluoroacetic acid (TFA), 1.53 ml of TFA is added to 2.5 ml of D.I. water on ice and the mixture is allowed to cool for ten minutes. 0.631 (13 mmol) of hydrazine hydrate is then slowly added on ice. After dissolution of the hydrazine the solution is warmed to room temperature and 0.531 g (5.0 mmol) of sodium bisulfite is added. The solution is then vortexed until all of the bisulfite has dissolved. The pH is adjusted to pH 7.1 using a combination of solid and 10 N NaOH and the volume adjusted to 5.0 ml with D.I. water. (2 pellets plus 5 to 10 drops 10N NaOH). A 100 mg/ml solution of hydroquinone in absolute ethanol is prepared and added to the bisulfite buffer at 50 ml of hydroquinone solution per 5 ml of bisulfite buffer.

Procedure: To a frozen sample of 300 mg of denatured salmon DNA in 300 ml of D.I. water is added 2.70 ml of the above buffer. One ml aliquots are placed in each of 3 tubes. Two tubes are incubated at 45 degrees in a water bath for 24 or 72 hrs. The third sample is then placed in 10 ml glass microwave tube and heated in a CEM microwave reactor at 45° C. with cooling for 1 hr.

After each reaction the sample is dialyzed against water several times. The DNA is recovered by iso-propanol precipitation and, after washing, dissolved in 50 ul water which is adjusted to 50 mM NaPO4 buffer pH 6.8 using a 1M stock. 100 ul of FITC (0.1M in DMSO) are added to each reaction followed by incubation at 60 degrees in a water bath for 16 hours. A modified procedure which involves 7 additional washes with Qiagen PB and 4 with Qiagen PE may also be used. DNA is eluted with Qiagen EB solution (2 aliquots of 50 ul.)

Spectra were taken and percentage of nucleotides labeled was calculated from OD 260 and OD 495. Results are shown in Table 2.

TABLE 2

16 Hour Thermal FITC Incorporation at 60° C. Following Thermal Hydrazinolysis at 45° C. for Various Times

|  | OD ($\lambda$ = 260 nm) | OD ($\lambda$ = 495 nm) | % Nuc. Labeled |
|---|---|---|---|
| 45 degrees 24 hr: | 0.57953 | 0.13448 | 5.5 |
| 45 degrees 72 hr: | 1.0058 | 0.5097 | 13.3 |

One hour in the microwave reactor gave as much labeling as 1 day in the water bath at the same temperature, which results can be seen by comparing the data in Table 2 with the data in Table 3 that follows in the next section.

Time Course in Microwave:

A reaction with 600 ug Salmon DNA and Bisulfite Hydrazine with TFA was set up in a single tube in the microwave at 45 degrees.

To prepare bisulfite with the chaotrope, trifluoroacetic acid (TFA), 1.53 ml of TFA was added to 2.5 ml of D.I. water on ice and the mixture was allowed to cool for ten minutes. 0.631 (13 mmol) of hydrazine hydrate was then slowly added on ice. After dissolution of the hydrazine the solution was warmed to room temperature and 0.531 g (5.0 mmol) of sodium bisulfite was added. The solution was then vortexed until all of the bisulfite had dissolved. The pH was adjusted to pH 7.1 using a combination of solid and 10 N NaOH and the volume adjusted to 5.0 ml with D.I. water. (2 pellets plus 5 to 10 drops 10N NaOH). A 100 mg/ml solution of hydroquinone in absolute ethanol was prepared and added to the bisulfite buffer at 50 ml of hydroquinone solution per 5 ml of bisulfite buffer.

Procedure: To a frozen sample of 600 mg of denatured salmon DNA in 300 ml of D.I. water was added 2.70 ml of the above buffer. The sample was then placed in 10 ml glass microwave tube and heated in a CEM microwave reactor at 45° C. with cooling. 0.5 ml samples were then removed and analyzed for labeling at the following time points; 5 minutes, 15 minutes, 30 minutes, 1 hour, 2 hours, and 3 hours.

Each aliquot was dialyzed against water and precipitated and washed as usual. After dissolving in 50 ul 50 mM NaPO4 buffer pH 6.8, 100 ul of an 0.1M FITC solution in DMSO was added prior to incubation at 60 degrees for 16 hr.

After purification on Qiagen minicolumns and washing, the spectra were taken and percent nucleotides labeled calculated for each time point. Result are shown in Table 3.

TABLE 3

16 Hour Thermal FITC Incorporation at 60° C. Following Microwave Hydrazinolysis at 45° C. for Various Times

| Time | Dilution | OD ($\lambda$ = 260 nm) | OD ($\lambda$ = 495 nm) | % Nuc Labeled |
|---|---|---|---|---|
| 5 Min | 1 to 10 | 1.1281 | 0.13075 | 2.648 |
| 15 Min | 1 to 2 | 1.2803 | 0.22278 | 4.05 |
| 30 Min | 1 to 2 | 1.2801 | 0.30014 | 5.58 |
| 1 hr | 1 to 2 | 0.58979 | 0.13545 | 5.45 |
| 2 hr | 1 to 2 | 1.32360 | 0.43956 | 8.18 |
| 3 hr | 1 to 2 | 1.85960 | 0.45943 | 5.9 |

Example 7

Time Course Microwave Experiments

Two time-course experiments to establish conditions for using the microwave reactor in bisulfite catalyzed coupling of hydrazine to natural DNA were conducted.

In the first experiment salmon DNA was reacted for various times and the hydrazine modified DNA was purified prior to reaction with a large excess of FITC. Based on measurements of the UV absorption spectrum, the percentage of modified nucleotides was calculated.

Figure 5:
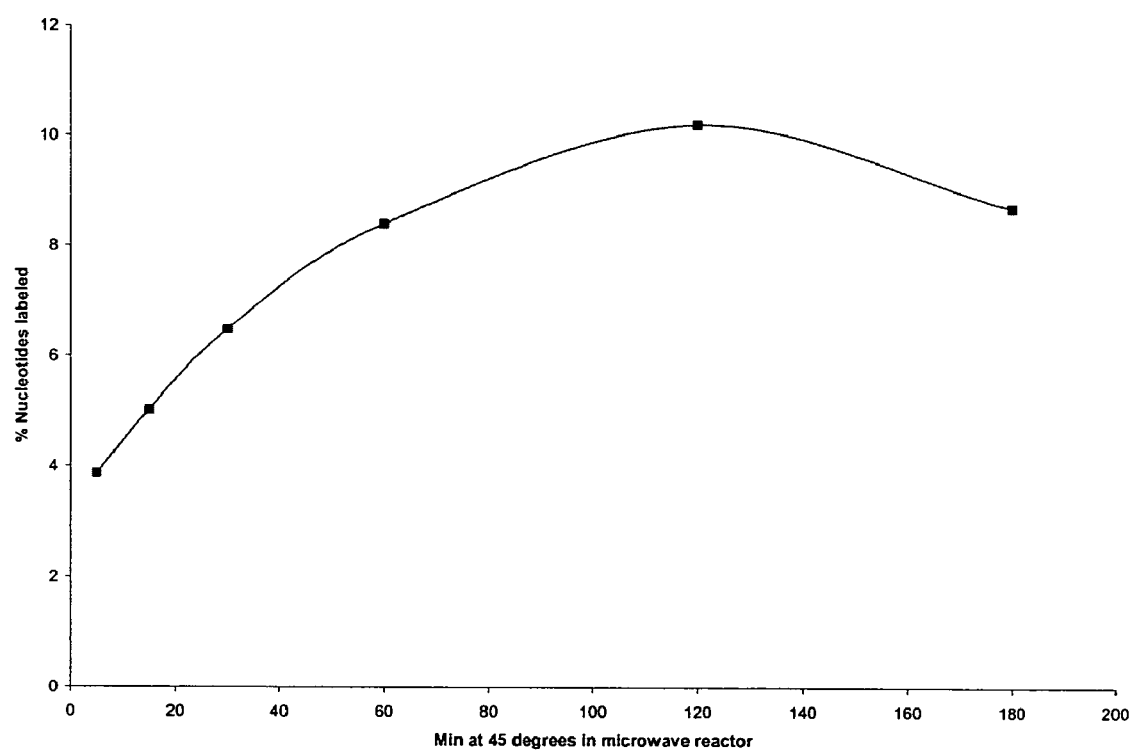
FIG. 5 is a chart showing FITC incorporation into DNA over time under microwave conditions.

In the second experiment, a mixture of HPV DNA's (corresponding to the High Risk probe cocktail) was reacted in the microwave for various times. The hydrazine modified DNA was purified and then reacted with a great excess of the active ester of a DNP-PEG linker (dinitrophenyl-polyethylene glycol compound described in Example 8). After extensive purification, the percentage of modified nucleotides was calculated as shown in FIG. 5.

The DNP labeled HPV DNA was used in ISH assays on slides. These 6 DNA preps were formulated as the standard probe except that initially their concentrations were double the standard concentration.

Interestingly, all 6 time points were more heavily DNP labeled than the standard probe (7 to 12% of the nucleotides vs about 2% for the standard probe. All 6 samples gave strong signal. Signal was visible in HeLa cells.

Example 8

Activation of Salmon DNA with Carbohydrazine ($H_2NHNCONHNH_2$)

To prepare bisulfite with the chaotrope, trifluoroacetic acid (TFA), 1.53 mL of TFA was added to 2.5 ml of D.I. water on ice and the mixture was allowed to cool for ten minutes. 1.17 g (13 mmol) of carbohydrizide was then slowly added on ice. After dissolution of the carbohydrizide the solution was warmed to room temperature and 0.531 g (5.0 mmol) of sodium bisulfite was added. The solution was then vortexed until all of the bisulfite had dissolved. The pH was adjusted to pH 7.1 using a combination of solid and 10 N NaOH (roughly 5 pellets and 3-7 drops of 10 N NaOH solution). The solution volume was adjusted to 5.0 mL with D.I., and 50 μL of 100 mg/mL hydroquinone in absolute ethanol was added.

Procedure: To a frozen sample of 400 μg of denatured salmon DNA in 300 μl of D.I. water was added 5.0 ml of the above buffer. The sample was then placed in 10 ml glass microwave tube and heated in a CEM microwave reactor at 45° C., 10 W, with cooling and stirring. 1.0 ml samples were then removed at the following time points; 15 minutes, 30 minutes, 1 hour, 2 hours, and 3 hours. The samples were dialyzed against D.I. water prior to precipitation with isopropanol and repeated washing with 80% ethanol.

The level of carbohydrizide incorporation into the DNA samples was assessed by labeling with fluorescein isothiocyanate. Each sample was dissolved in 50 mL of 50 mmol phosphate buffer pH 7.5, and then treated with 200 μL of 0.1 M fluorescein isothiocyanate in DMSO. Samples were incubated in a water bath at 60° C. for 16 hours. The DNA was then recovered by repeated precipitation and washing with 80% ethanol. The level of fluorescein incorporation was then determined by comparing the measured absorbance's at 260 nm and 495 nm. The data are shown below.

| Time in Minutes | 15 | 30 | 60 | 120 | 180 |
|---|---|---|---|---|---|
| Percent FTIC Incorporation | 18.365 | 17.39 | 18.7 | 20.678 | 16.3 |

Example 9

Synthesis of 3(2(2(2(2(2,4-dinitrophenyl-amino) ethoxy)ethoxy)ethoxy)ethoxy)propanoic Acid (1)

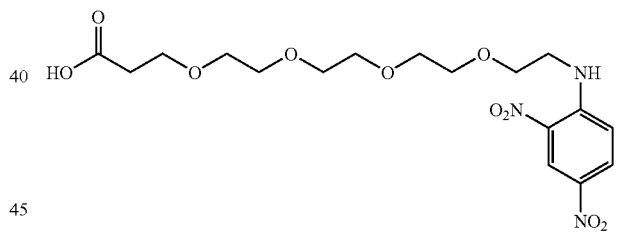

3-(2-(2-(2-(2-(2-aminoethoxy)ethoxy)-ethoxy)ethoxy) propanoic acid (1.0 g, 3.77 mmol) was suspended in 5 mL of anhydrous DMF, and to this suspension was added (0.47 mL, 3.77 mmol) of 1-fluoro-2,4-dinitrobenzene. The mixture was then vortexed until all of the amino acid had dissolved and then shaken at ambient temperature under dry nitrogen for sixteen hours. The solvent was removed in vacuo and the residue was purified by silica gel chromatography utilizing an Isco combiflash automated chromatography unit (MeOH/$H_2O$, 10-50% MeOH over 25 minutes) to afford the aniline as yellow oil (948 mg, 58%). $^1$H NMR (250 MHz, CDCl$_3$) δ 2.58 (t, J=6.0 Hz, 2H), 3.57-3.84 (m, 18H), 6.94 (d, J=9.5 Hz, 1H), 8.25 (dd, J=9.5, 2.6 Hz, 1H), 8.81 (br s, 1H), 9.12 (d, J=2.7, 1H); $^{13}$C NMR (500 MHz, CD$_3$OD) δ 36.0, 44.2, 67.9, 70.0, 71.5, 71.6, 71.71, 71.72, 71.74, 71.77, 116.2, 124.8, 131.1, 131.6, 137.1, 150.0, 175.4; ESI-MS m/z 432(M+H); FAIB-HRMS calcd for $C_{17}H_{25}N_3O_{10}$ (M+Na) 454.1438, found 454.1438.

Synthesis of 3(2(2(2(2(2,4dinitrophenylamino)ethoxy)ethoxy)ethoxy)ethoxy)-propanate-N-hydroxysuccinimide ester (2)

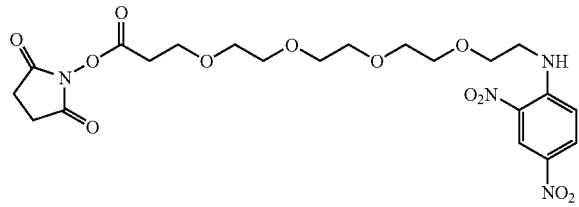

The acid (1) (748 mg, 1.73 mmol) was dissolved in 1.9 mL of anhydrous DMF and to this solution was added 1.0 M DCC in DCM (1.92 mL, 1.92 mmol), triethylamine (289 µl, 2.08 mmol), and N-hydroxysuccinimide (221 mg, 1.92 mmol). The solution was then blanketed with dry argon and shaken at ambient temperature for 16 hours. The solvent was removed in vacuo and the residue taken up in dry DCM. After filtering away the urea byproduct, the active ester was purified by silica gel chromatography utilizing an Isco combiflash automated chromatography unit. $^1$H NMR (250 MHz, CDCl$_3$) δ 2.90 (t, J=6.5 Hz, 2H), 3.57-3.70 (m, 14H), 3.79-3.84 (m, 4H), 6.94 (d, J=9.6 Hz, 1H), 8.25 (td, J=9.5, 1.4, 1H), 8.81 (br s, 1H), 9.12 (d, J=2.6 Hz, 1 H);

Example 10

Synthesis of $N^4$-amino-deoxycitidine 5'-triphosphate (3)

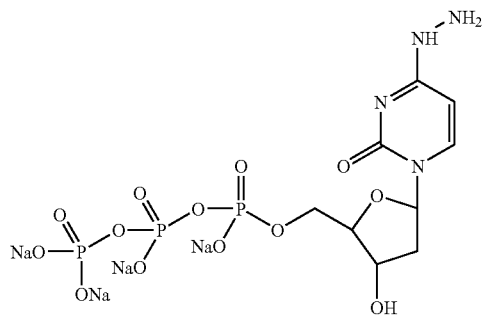

In a 50 mL glass scintillation vial 50 mg of sodium bisulfite (0.468 mmol) was dissolved in 200 µl of D.I. water. The solution was then placed on an ice bath and 760 µl of hydrazine hydrate (15.65 mmol) was slowly added. Following the hydrazine addition, the pH was immediately adjusted to 7.1 with concentrated HCl. In a 10 mL glass microwave reaction tube was added 200 mg of cytidine 5'-triphosphate and the pre-made hydrazine/bisulfite solution. The tube was vortexed until all of the cytidine 5'-triphosphate had dissolved and then heated in a CEM Discover microwave reactor at 55° C. for 1 hr. The reaction mixture was fractionated by HPLC utilizing a Waters Delta 600 HPLC fitted with a 2996 photo-diodarray detector and a Phenomenex luna 10µ, C18(2), 100 A, 250×30 mm column (350 µl reaction mixture per run). The column was eluted with 125 mM triethylammonium carbonate, 1-4% ACN over 20 minutes at a pH of 8.5 and a flow rate of 12 mL/min. The $N^4$-am-dCTP fraction eluted at 28 minutes with λmax at 274.5 nm and a purity of 84% as measured by absorbance at 270 nm. The $N^4$-am-dCTP fraction was lyophilized 3 times to ensure removal of all residual triethylammonium carbonate and then stored at −80° C. until exchange of the triethylammonium cation for sodium. Cation exchange was performed on a 50 mL column packed with Sp sephadex C-25 equilibrated with 0.2 N NaOH then washed with D.I. water until the pH of the eluting buffer was 7.0. The lyophilized triethylammonium salt was taken in 1 mL (4×0.250 mL) of D.I. water loaded on top of the cation exchange column and eluted with D.I. water. The uv/vis spectrum of the collected fractions was measured on an Agilent 8453 UV/VIS spectrophotometer, and the $N^4$-am-dCTP containing fraction were pooled and lyophilized to give 120 mg of the tetra-Na salt of $N^4$-am-dCTP as a white crystalline solid.

Synthesis of $N^4$-amino-deoxycytidine 5'-triphosphate-PEG$_4$-DNP (4)

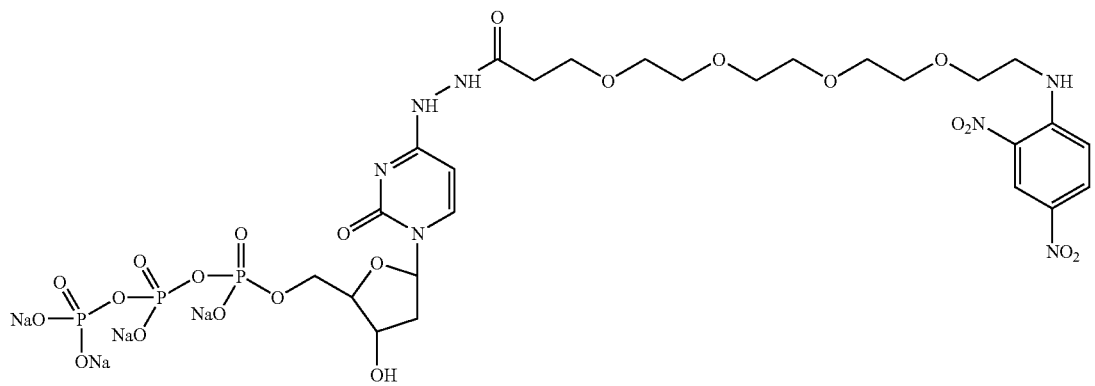

In a 10 mL amber glass vial 173 mg of the tetra-triethylammonium salt of (3) (0.195 mmol) was dissolved in 1.5 ml of anhydrous DMF. To this solution was added 124 mg of the active ester (2) in 2 ml of dry DMF (0.234 mmol). The solution blanketed with dry argon and vortexed until all solids had dissolved. The reaction was then shaken at ambient temperature for 16 hours. The reaction mixture was fractionated by HPLC utilizing a Waters Delta 600 HPLC fitted with a 2996 photo-diodarray detector and a Phenomenex luna 10μ, C18(2), 100 A, 250×30 mm column (250 μl reaction mixture per run). The column was eluted with 125 mM triethylammonium carbonate, 25% ACN at a pH of 8.5 and a flow rate of 15 mL/min. The $N^4$-am-dCTP-PEG-DNP fraction eluted at 22 minutes with a λ max at 358.5 nm and a purity of 67% as measured by absorbance at 360 nm. The $N^4$-am-dCTP-PEG-DNP fraction was lyophilized 3 times to ensure removal of all residual triethylammonium carbonate and then stored at −80° C. until exchange of the triethylammonium cation for sodium. Cation exchange was performed on a 50 mL column packed with Sp sephadex C-25 equilibrated with 0.2 N NaOH then washed with D.I. water until the pH of the eluting buffer was 7.0. The lyophilized triethylammonium salt was taken in 1 mL (4×0.250 mL) of D.I. water loaded on top of the cation exchange column and eluted with D.I. water. The uv/vis spectrum of the collected fractions was measured on an Agilent 8453 UV/VIS spectrophotometer, and the $N^4$-am-dCTP-PEG-DNP containing fractions were pooled and lyophilized to give 115 mg of the tetra-Na salt of $N^4$-am-dCTP as a yellow crystalline solid. $^1$H NMR (250 MHz, $D_2O$) δ 2.27 (m, 1H), 2.36 (br m, 1 H), 2.63 (t, J=4.8 Hz, 2H) 3.85-3.63 (m, 18H), 4.18 (d, J=4 Hz, 3H), 4.58 (br s, 1 H), 6.19 (br s, 2H), 7.15 (d, J=8 Hz), 7.94 (br s, 1H), 8.27 (d, J=8.3 Hz, 1H), 9.04 (s, 1H); $^{13}$C NMR (500 MHz, $D_2O$) δ 34.4, 39.8, 42.8, 65.47, 65.51, 66.62, 68.82, 69.94, 70.02, 70.06, 70.10, 70.72, 71.94, 85.98, 86.37, 92.7, 115.4, 124.9, 130.3, 130.8, 135.7, 141.7, 143.6, 149.3, 173.2, 173.6; $^{31}$P NMR (300 MHz, $D_2O$) δ-8.39 (d, J=41 Hz, 1 P), 10.58 (d, J=48 Hz, 1P), −22.00 (t, J=48 Hz, 1P); ESI-MS m/z 984.1 (M+H); FAB-HRMS calcd for $C_{17}H_{25}N_3O_{10}$ (M+H) 984.0795, found 984.0795.

Example 11

DNA Labeled with $PEG_4$-bis-hydrazine-DNP

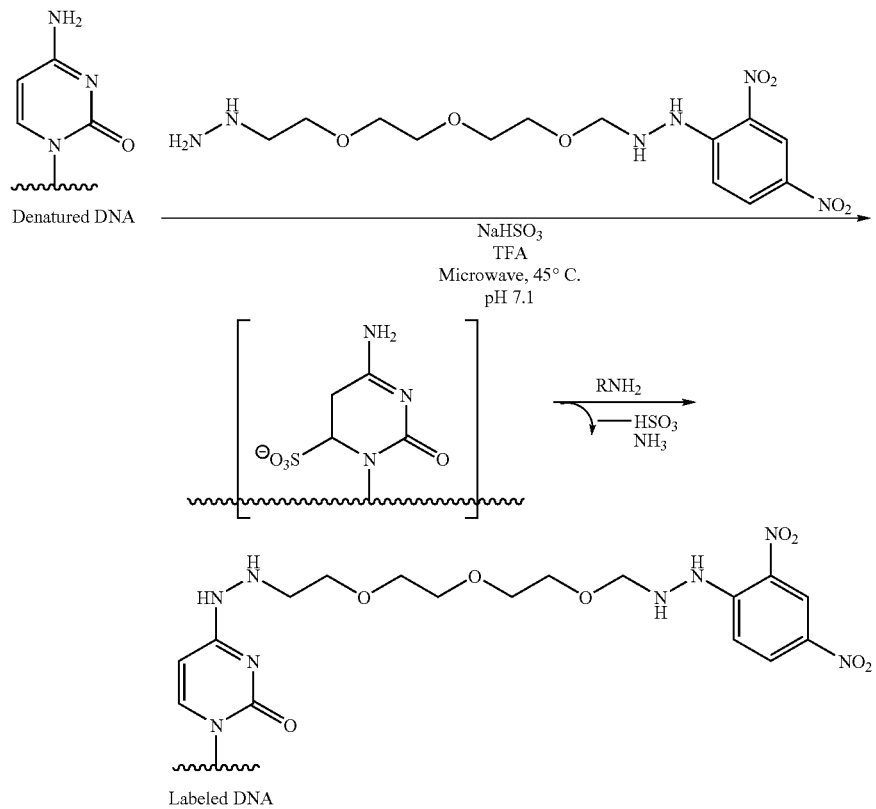

Synthesis of $Peg_4$-bis-hydrazine

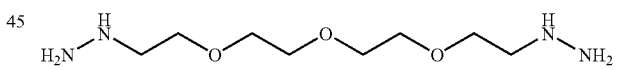

A dry 1 L round bottom flask was charged with 50 g (230 mmol) of tetraethylene glycol, 128 mL of triethylamine (920 mmol), and 200 mL of anhydrous DCM. The flask was immersed in an ice bath, and 54 mL mesylchloride was added over 4 hours under dry nitrogen. The reaction was then brought to ambient temperature and allowed to stir for 18 hours. The crude reaction was filter to remove the amine salts and the solvent removed under vacuum to give the crude mesylate as viscous brown oil.

The crude mesylate was taken up in 100 mL of anhydrous DCM and the solution dripped into hydrazine hydrate (2.3 mol) in 100 mL of dry THF over 5 hours. The reaction was then allowed to stir at ambient temperature under dry nitrogen for 16 hours. The excess hydrazine and solvent were removed under vacuum to give the bis-hydrazine product as an amorphous light yellow solid. Repeated titiration with cold methanol afforded 42.5 g of the final $Peg_4$-bis-hydrazine product as white needles. ESI-MS m/z calcd for $C_8H_{22}N_4O_3$ 222.2, found 222.2.

Synthesis of hydrazine-PEG₄-DNP

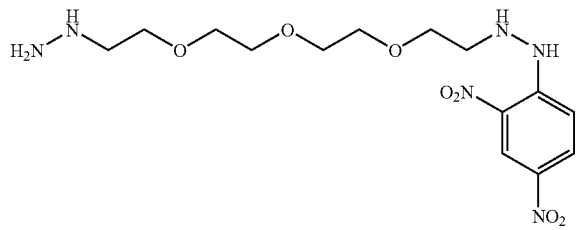

In a 25 ml round bottom flask was added 710 mg (3.2 mmol) of the bis-hydrazine-PEG₄ linker in 3 ml of dry DMSO. Into this solution, over 1 hour, was dripped a solution of 74 µl (0.32 mmol) of Sangers reagent in 3 ml dry DMSO. The reaction was allowed to stir for an additional 1 hour at ambient temperature under dry nitrogen, and then fractionated by preparative HPLC utilizing a Waters Delta 600 HPLC fitted with a 2996 photo-diodarray detector and a Phenomenex luna 10µ, C18(2), 100 A, 250×30 mm column (500 µl reaction mixture per run). The column was eluted with 40-60% MeOH/water over 20 minutes at a flow rate of 12 mL/min. The bis-hydrazine-PEG₄-DNP fraction eluted at 34 minutes with a λ max at 358.5 nm.

Example 12

Synthesis of Polyacrylamide Hydrazide

In a 100 mL round-bottom flask fitted with a condenser, 20 mL polyacrylamide (1 mmol, 50% wt in water, Sigma-Aldrich, Milwaukee, Wis.) was mixed with 10 mL distilled (DI) water and 20 mL hydrazine monohydrate (420 mmol, Sigma-Aldrich, Milwaukee, Wis.). The reaction was microwaved in a CEM Discovery unit for 60 min. After cooling to room temperature, the reaction was precipitated with an equal volume of methanol, centrifuged and decanted. The residue was taken up in 50 mL DI water and the precipitation repeated for a total of three times. The final residue was dissolved in DI water and lyophilized to give a fine, white hygroscopic powder.

The invention has been described with reference to various specific and preferred embodiments and techniques. However, it should be understood that many variations and modifications may be made while remaining within the spirit and scope of the invention.

20. The compound of claim 19 having the structure:
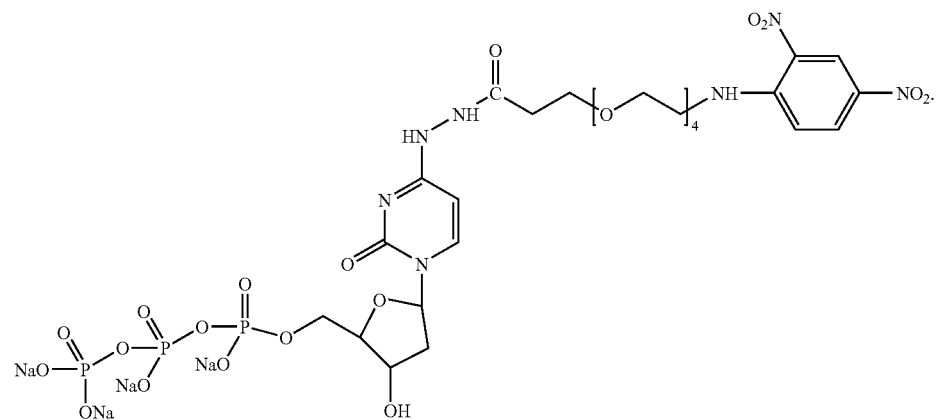

What is claimed is:

1. A method for conducting a bisulfite-catalyzed reaction of a compound, the compound selected from the group consisting of cytosine, cytidine, deoxycytidine, cytidine triphosphate, deoxycytidine triphosphate, cytidylate, deoxycytidylate, and a polynucleotide comprising cytidine or deoxycytidine, the method comprising the steps of:

activating a C4 amino group of a cytosine ring of the compound by reacting the compound with bisulfite to form a bisulfite adduct of the compound having the structure:

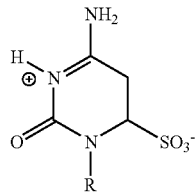

(II)

wherein R is H, ribosyl, 2'-deoxyribosyl, ribosyl-5'-phosphate, 2'-deoxyribosyl-5'-phosphate, ribosyl-5'-triphosphate, 2'-deoxyribosyl-5'-triphosphate, a ribosyl-5'-phosphate moiety of a polyribonucleotide or a 2'-deoxyribosyl-5'-phosphate moiety of a polydeoxyribonucleotide; and contacting the adduct with a nucleophile, thereby displacing the amino group with the nucleophile, the nucleophile selected from the group consisting of H₂NNH₂, NH₂OH, H₂NNHCONH₂, H₂NNHCSNH₂, H₂NNHCONH₂NH₂, H₂NNHCSNH₂NH₂, H₂NNH—Y1-Q-Y2-NHNH₂, H₂N—REP, H₂NNH—REP, H₂NNHCO—REP, H₂NNHCS—REP, H₂NNHCONH—REP, H₂NNHCSNH—REP, H₂NNHCONHNH—REP, H₂NNHCSNHNH—REP, H₂N-L-REP H₂NNH-L-REP, H₂NNHCO-L-REP, H₂NNHCS-L-REP, H₂NNHCONH-L-REP, H₂NNHCSNH-L-REP, H₂NNHCONHNH-L-REP, H₂NNHCSNHNH-L-REP, H₂NNH—Y1-Q-Y2-REP, and H₂NNH—Y1-Q-Y2-NHNH-REP; wherein Y1 and Y2 are independently a bond or —C(O)—; Q is —(OCH₂CH₂)ₙ—, wherein n is 2 to 30; L is a bond or a linker group, the linker group comprising a linear repeating oxyalkyl group, a branched repeating oxyalkyl group, a linear aliphatic group, a mixed aliphatic-aromatic group, an aromatic group, an alicyclic group, a heteroaromatic group, or a heteroalicyclic group; and REP is a detectable reporter group; and wherein said activating step, said contacting step, or both, are conducted in the presence of microwave energy having a wavelength of between 1 mm and 1 meter and said bisulfite-catalyzed reaction is accelerated at a given temperature relative to said bisulfite-catalyzed reaction conducted at the same temperature in the absence of said microwave energy.

2. The method of claim 1 wherein the nucleophile is selected from the group consisting of H₂N-L-REP, H₂NNH-L-REP, H₂NNHCO-L-REP, H₂NNHCS-L-REP, H₂NNHCONH-L-REP, H₂NNHCSNH-L-REP, H₂NNHCONHNH-L-REP, and H₂NNHCSNHNH-L-REP; wherein L is a bond or a linker group, the linker group comprising a linear repeating oxyalkyl group, a branched repeating oxyalkyl group, a linear aliphatic group, a mixed aliphatic-aromatic group, an aromatic group, an alicyclic group, a heteroaromatic group, or a heteroalicyclic group, and REP is a detectable reporter group; and the bisulfite-catalyzed reaction produces a compound having the formula:

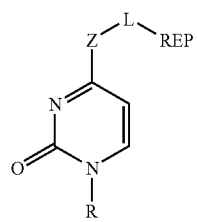

(I)

wherein, R is H, ribosyl, 2'-deoxyribosyl, ribosyl-5'-phosphate, 2'-deoxyribosyl-5'-phosphate, ribosyl-5'-triphosphate, 2'-deoxyribosyl-5'-triphosphate, a ribosyl-5'-phosphate moiety of a polyribonucleotide or a 2'-deoxyribosyl-5'-phosphate moiety of a polydeoxyribonucleotide, and Z-L-REP is HN-L-REP, HNNH-L-REP, HNNHCO-L-REP, HNNHCS-L-REP, HNNHCONH-L-REP, HNNHCSNH-L-REP, HNNH-CONHNH-L-REP, or HNNHCSNHNH-L-REP.

3. The method of claim 2 wherein L is —(OCH$_2$CH$_2$)$_n$—, wherein n is 2 to 30.

4. The method of claim 2 wherein REP is a 2,4-dinitrophenyl moiety, a fluorescein moiety or a biotin moiety.

5. The method of claim 1, wherein REP is a fluorophore, a chromogen, a hapten, an enzyme, a nanoparticle, or a quantum dot.

6. The method of claim 5, wherein REP is a fluorophore or a hapten.

7. The method of claim 1, wherein the nucleophile is selected from the group consisting of H$_2$NNH$_2$, H$_2$NNHCONH$_2$, H$_2$NNHCSNH$_2$, H$_2$NNHCONH$_2$NH$_2$, H$_2$NNHCSNH$_2$NH$_2$, and H$_2$NNH—Y1-Q-Y2-NHNH$_2$; wherein Y1 and Y2 are independently a bond or —C(O)—, Q is —(OCH$_2$CH$_2$)$_n$—, and wherein n=2 to 30; and the bisulfite-catalyzed reaction produces a compound having the formula (IV-A):

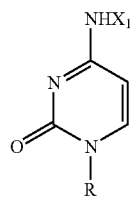

(IV-A)

wherein R is H, ribosyl, 2'-deoxyribosyl, ribosyl-2'5-phosphate, 2'-deoxyribosyl-5'-phosphate, ribosyl-5'-triphosphate, 2'-deoxyribosyl-5'-triphosphate, a ribosyl-5'-phosphate moiety of a polyribonucleotide or a 2'-deoxyribosyl-5'-phosphate moiety of a polydeoxyribonucleotide, and X$_1$ is —NH$_2$, —NHCONHNH$_2$, —NHCSNHNH$_2$, —NHCSNH$_2$, —NH-CONH$_2$, —NH-Q-NHNH$_2$ or —NH—Y1-Q-Y2-NHNH$_2$, where Y1 and Y2 are independently a bond or —C(O)— and Q is —(OCH$_2$CH$_2$)$_n$—, where n is 2 to 30.

8. The method of claim 7, wherein the nucleophile is NH$_2$NH$_2$, the compound is cytidine 5'-triphosphate or deoxycytidine 5'-triphosphate and the bisulfite-catalyzed reaction forms a N$^4$-amino-cytidine 5'-triphosphate or a N$^4$-amino-deoxycytidine 5'-triphosphate.

9. The method of claim 1, wherein the nucleophile is H$_2$NNH—Y1-Q-Y2-NHNH-REP; wherein Y1 and Y2 are independently a bond or —C(O)—; Q is —(OCH$_2$CH$_2$)$_n$—, wherein n is 2 to 30; and REP is a hapten.

10. The method of claim 1 wherein the nucleophile is selected from the group consisting of H$_2$NNH$_2$, H$_2$NNHCONH$_2$, H$_2$NNHCSNH$_2$, H$_2$NHCONHNH$_2$, H$_2$NHCSNHNH$_2$, and H$_2$NNH—Y1-Q-Y2-NHNH$_2$, NH$_2$OH, wherein Y1 and Y2 are independently a bond or —C(O)—; Q is —(OCH$_2$CH$_2$)$_n$—, wherein n is 2 to 30; and the bisulfite-catalyzed reaction produces a compound of formula (IV):

(IV)

wherein R is H, ribosyl, 2'-deoxyribosyl, ribosyl-5'-phosphate, 2'-deoxyribosyl-5'-phosphate, ribosyl-5'-triphosphate, 2'-deoxyribosyl-5'-triphosphate, a ribosyl-5'-phosphate moiety of a polyribonucleotide or a 2'-deoxyribosyl-5'-phosphate moiety of a polydeoxyribonucleotide, and X is —NH—, —NHCONH—, —NHCSNH—, —NHCONHNH—, —NHCSNHNH—, —NH—Y1-Q-Y2-NHNH—, or —O—.

11. A compound of formula (IV-A):

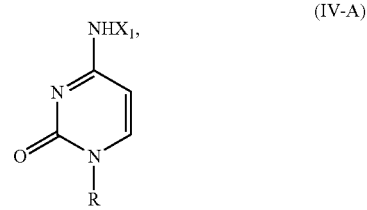

(IV-A)

wherein R is H, ribosyl, 2'-deoxyribosyl, ribosyl-5'-phosphate, 2'-deoxyribosyl-5'-phosphate, ribosyl-5'-triphosphate, 2'-deoxyribosyl-5'-triphosphate, a ribosyl-5'-phosphate moiety of a polyribonucleotide or a 2'-deoxyribosyl-5'-phosphate moiety of a polydeoxyribonucleotide; and X$_1$ is —NH-CONHNH$_2$, —NHCSNHNH$_2$, —NH-Q-NHNH$_2$ or —NHCO-Q-CONHNH$_2$ where Q is —(OCH$_2$CH$_2$)n-, where n is 2 to 30.

12. A compound having the formula:

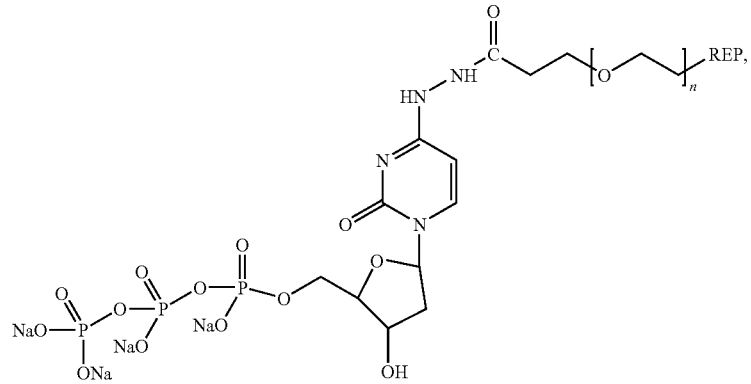

wherein, n=2 to 30 and REP is a detectable reporter group or a hapten.

13. The compound of claim 12, wherein REP is a hapten.

14. A method for conducting a bisulfite-catalyzed reaction, comprising:

activating a C4 amino group of deoxycytidine-5'-triphosphate by reacting the deoxycytidine-5'-triphosphate with bisulfite to form a bisulfite adduct of deoxycytidine-5'-triphosphate having the formula:

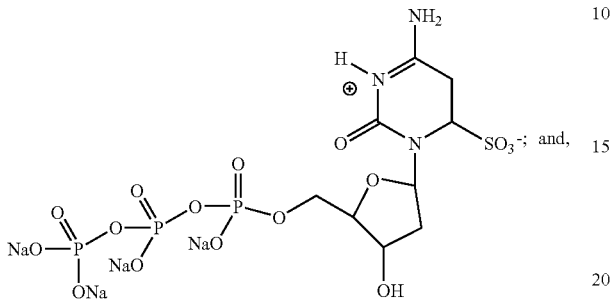

contacting the adduct of deoxycytidine-5'-triphosphate with hydrazine, thereby displacing the activated amine group with the hydrazine to form $N^4$-amino-deoxycytidine-5'-triphosphate, wherein said activating step, said contacting step, or both, are conducted in the presence of microwave energy having a wavelength of between 1 mm and 1 meter and said bisulfite-catalyzed reaction is accelerated at a given temperature relative to said bisulfite-catalyzed reaction conducted at the same temperature in the absence of said microwave energy.

15. The method of claim 14 further comprising reacting the $N^4$-amino-deoxycytidine-5'-triphosphate with a compound having the formula:

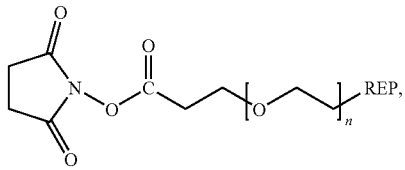

wherein n=2 to 30 and REP is a detectable reporter group or a hapten to produce a compound of the formula:

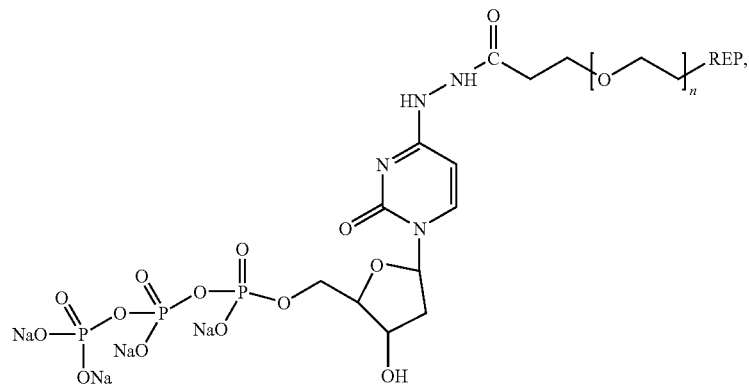

wherein, n=2 to 30 and REP is a detectable reporter group or a hapten.

16. The method of claim 15, wherein REP is a hapten.

17. The method of claim 16, wherein the hapten is a 2,4-dinitrophenyl moiety.

18. The method of claim 15, wherein n=4 and REP is a 2,4-dinitrophenyl moiety.

19. The compound of claim 12 having the structure:

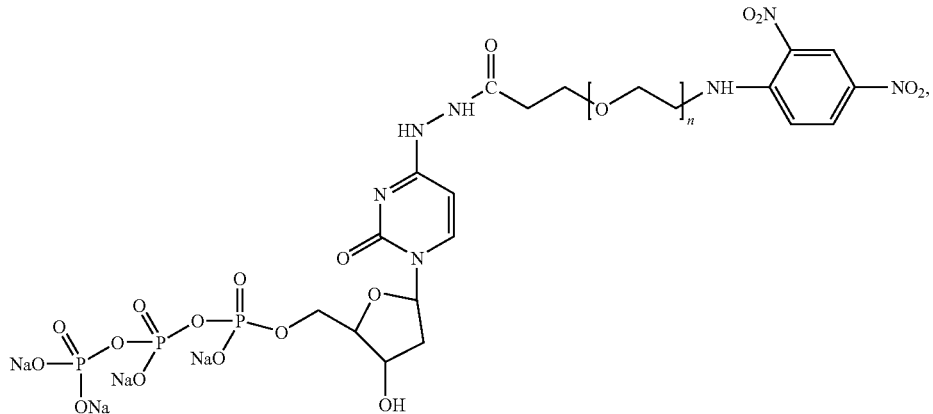

wherein n 2 to 30.